United States Patent [19]

Saunders et al.

[11] Patent Number: 5,208,166
[45] Date of Patent: May 4, 1993

[54] REACTIVE CHITOSAN COATED ARTICLES AND TEST KIT FOR IMMUNOASSAY

[76] Inventors: Mary S. Saunders, Rte. 3, Box 106-1, Monticello, Fla. 32344; Randall K. Pegg, 5201 First Coast Hwy., Amelia Island, Fla. 32034

[21] Appl. No.: 662,420

[22] Filed: Feb. 28, 1991

[51] Int. Cl.$^5$ .......................................... G01N 33/544
[52] U.S. Cl. ...................... 436/518; 422/57; 422/61; 427/2; 427/337; 427/338; 427/414; 436/528; 436/529; 436/808; 436/809; 514/55; 536/20
[58] Field of Search .................. 422/57, 58, 61; 427/337–339, 414, 415, 2; 435/7.33; 436/518, 528, 805, 807, 808, 809, 529; 514/55; 536/20, 55.3

[56] References Cited

U.S. PATENT DOCUMENTS

| | | | |
|---|---|---|---|
| 4,167,447 | 9/1979 | Masri et al. | 435/178 |
| 4,326,532 | 4/1982 | Hammar | 428/411.1 |
| 4,471,058 | 9/1984 | Smith et al. | 436/548 |
| 4,681,782 | 7/1987 | Ozkan | 436/807 |
| 4,879,340 | 11/1989 | Moriguchi et al. | 536/20 |
| 4,929,722 | 5/1990 | Partain et al. | 514/55 |
| 4,938,998 | 7/1990 | Stock | 428/413 |
| 4,942,129 | 7/1990 | Goosen et al. | 435/182 |

FOREIGN PATENT DOCUMENTS

| | | | |
|---|---|---|---|
| 2288602 | 12/1987 | Japan | 536/20 |

*Primary Examiner*—David Saunders
*Assistant Examiner*—Christopher L. Chin
*Attorney, Agent, or Firm*—R. Kevin Pegg

[57] ABSTRACT

A reagent coating material has been developed to modify the surface of articles used in assay procedures. Polymers of chitosan solubilized with an organic acid form into thin films when contacted to glass, plastic, metal or cellulose articles. The coated article may be used directly for immobilizing agents for assay, or may be further modified to increase the range of usefulness. The reagent coating solution itself may also be reacted to produce an activated reagent with surface coating properties. The invention embodies a kit of use in immunoassay procedures.

9 Claims, No Drawings

REACTIVE CHITOSAN COATED ARTICLES AND TEST KIT FOR IMMUNOASSAY

BACKGROUND OF THE INVENTION

1. Field of the Invention

This invention relates to the development of a novel composition having surface coating properties useful in immunoassay procedures. More particularly this invention relates to development of a kit combining reagents and a method to produce immunochemical devices having highly defined reactive surface properties. The system employs a formulation of chitosan and an organic acid to coat plastic microtiter wells. The chitosan is fixed with an alkaline solution to produce a thin film insolubilized on the plastic. Concomitant with fixation, mild oxidation of the surface coating produces highly reactive groups that will bind antigen or antibody to the wells of the microtiter plate.

2. Background Information

The monitoring of medically important substances and foreign substances in the environment has become increasingly dependent on immunoassay technology. Antibody directed against a molecule has the ability to act as a reagent for the estimation of its target molecule in a fluid sample. Immunoassay technology is a widely practiced art. In general the assay requires immobilization of either antibody or antigen to an insoluble surface (substrate). The reaction proceeds with the addition of reagents, and the formation of an antibody/antigen complex. Antibody binding can then be measured by colorimetric, radiometric, turbidometric, and fluorometric means.

A variety of immunochemical substrates exist including materials such as metal, cellulose, glass, and plastic. Substrates may take the form of tubes, beads, filters, dipsticks, and particles. The most widely practiced art is the microtiter well formed in plastic. These devices are formed of any plastic including polystyrene, polycarbonate, polypropylene, or polyvinyl chloride. Typically these devices are in strips of either eight or twelve wells ganged together, or in plates of up to 96 wells. The plastic may act as the substrate, or the microtiter well manufactured with an added ingredient to increase the binding of agents to the surface. An example is found in U.S. Pat. No. 4,657,873 (Gadero, 1987) which describes activating plastic surfaces with a phenyllysine copolymer to provide a surface for subsequent crosslinking reactions. The consistency and uniformity of these coatings directly impact the performance of the test.

A variety of strategies to further increase the reactivity of microtiter wells are available to practioners of this art. These include coatings of bovine serum albumin, poly-1-lysine, polyacrylamide, alginate, carrageenan, and others. See, p. Tijssen, PRACTICE AND THEORY OF ENZYME IMMUNOASSAYS, LABORATORY TECHNIQUES IN BIOCHEMISTRY AND MOLECULAR BIOLOGY (1985). The goal of coating solutions in immunoassay test procedures is to increase and control the binding of reactants. Desired traits of solid phase coatings include: high ligand capacity, diversity of immunoreactants, minimal dissociation, negligible denaturation of antigen or antibody, controlled orientation, inexpensive, uniform, controlled spacing of epitopes and paratopes, minimal interaction between coating and secondary regents, no binding effects (background) or steric hindrance, immunochemically transparent, and negligible optical interference. Bovine serum albumin is the most widely employed reagent in coating technology. Absoption of albumin to plastic microtiter plates varies considerably between types of plastics. There is considerable lot to lot variation of both microtiter plates and albumin. The pH of the binding solution is also a factor that results in decreased absorption. Considerable assay to assay variability will occur from the use of albumin coatings. Additionally, the small number of amine bearing lysine residues limits subsequent coupling via bridging molecules such as glutaraldehyde.

Poly-1-lysine offers greater sensitivity for coupling reactions, however considerable non-specific binding occurs. Membranes and particles of chitosan, a copolymer of glucosamine and galactosamine derived by hydrolysis of chitin, have been used as a support in immunoassay procedures after the material was crosslinked into an insoluble substrate. The poly hexosamine chitosan, a derivative of chitin, has been the subject of numerous reviews (CHITIN, CHITOSAN AND RELATED ENZYMES, 1984, ACADEMIC PRESS INC.). Chitosan has been analyzed using sodium nitrite in a general method for determination of mucopolysaccarides (Tsuji et al., 1969; Clin. Pharm. Bull. 17:1505). Chitosan has been used as an immobilizing agent for enzymes and other biological proteins. U.S. Pat. No. 4,167,447 (Masri et al., 1979) describes a precipitation procedure for insolubilization of chitosan and macromolecules using alkaline conditions. U.S. Pat. No. 4,089,746 (Masri et al., 1978) insolubilized enzymes on chitosan gels using a crosslinking agent. U.S. Pat. No. 4,094,743 (Leuba, 1978) used chitosan flakes and powders as a support with a dialdehyde crosslinker. U.S. Pat. No. 4,760,024 (Lantero, 1988) produced a spherical aggregate of chitosan and enzymes using glutaraldehyde. The technology cited above require crosslinking of the chitosan with glutaraldehyde to stabilize the chitosan and provide reactive areas.

Each of the foregoing technologies meets at least one of the goals for an optimal reactive coating but each also contain features that compromise the technology. Serum albumins are not immunochemically transparent and may result in background staining. Polylysine and its various copolymers result in nonspecific binding interactions. Passive absorption to unmodified plastics results in nonuniformity. Thus, a need continues to exist for a reliable and cost effective material for immobilization.

SUMMARY OF THE INVENTION

The immunoassay system of the instant invention comprises a substrate and novel coating material. The coating material may be derivatized to form a hapten coating or the coating may be activated by additional reagents to produce a reactive surface.

In accordance with one object of the invention a substrate formed as a microtiter well is contacted with the coating solution to form a coating that will enhance the binding of a dissolved protein to the substrate. The substrate may be derived of glass, plastic, cellulose, or metal and may be shaped. Preferentially, the substrate is a plastic microtiter well made from polystyrene, polyethylene, polycarbonate, polypropylene, or polyester, or a combination.

In accordance with another object of the invention the substrate coating is a hexosamine such as chitosan.

A particularly novel feature of this invention is the ability of a chitosan coated article to be activated. Through this aspect of the invention the chitosan coating is oxidized to form a reactive coating that will bind the primary amines and alcohols of proteins and hapten organic molecules to form a covalent bond thereby increasing the amount of bound material on the substrate. The addition of oxidizers such as sodium nitrite or sodium hypochlorite will produce a reactive surface that can covalently bind protein, nucleic acids, haptens, and other molecules for subsequent assay. The system allows a wide variety of protein and peptide antigens to be coupled in this manner. Proteins include, but are not limited to antibody, enzyme, structural proteins, membrane proteins, gene products, and synthetic proteins. A particularly novel feature of this invention is the ability of the device to immobilize proteins dissolved in a surfactant. Peptide antigens may be similarly attached. These molecules include peptide hormones such as oxytosin, neuropeptides, angiotensin, interleukins, T-cell peptides, and any other natural or synthetic peptide having a free amine or hydroxyl of interest to practioners of the immunoassay art.

In yet another feature the system described herein is used to immobilize haptens as a surface coating. Haptens are made reactive by producing reactive analogs, such as hydroxysuccinimide activated carboxylate derivatives. The activated hapten is added to a solution of the chitosan to derivatize it prior to surface coating. Haptens that may be bound include drugs or drug analogs such as cannabinoid, morphines, barbituates, sulfa drugs, steroids, estrogens, amphetamines, gentamycin, neomycin, tobramycin and others. Haptens of environmental interest include dioxin, halogenated hydrocarbons, phenolic compounds, pesticides, and industrial residue.

Another novel feature is the ability of the reagents to be combined in a kit comprising a solution of chitosan in citrate buffer, and in a separate vessel, reagents for preparation of sodium nitrite oxidizer. This will enable the end user to chemically bind most proteins, antigens, and haptens to substrates that suit their individual needs.

DETAILED DESCRIPTION OF THE PREFERRED EMBODIMENTS

Objects of the invention achieved by providing an apparatus and method for use in immunoassay procedures comprise: A) a substrate for immobilization, comprising plastic, glass or metal; B) a coating solution comprising chitosan and a polyvalent organic acid, preferably citric acid; C) an activating solution comprising an oxidizing agent such as sodium nitrite.

In a further embodiment of the invention a chitosan coated article may be reacted with an activated hapten to form a stable covalent complex of chitosan-hapten. This material may be substituted for the chitosan coating solution to produce a surface bearing the hapten in high concentrations.

In yet another aspect of the present invention provides the reagent and method as a kit for the coupling of proteins and haptens. The kit comprises a chitosan solution and in a separate container the oxidizing solution. This kit allows the end user to create substrates having properties unique to an individual application.

The substrate may be derived of glass, plastic, cellulose, or metal and may be shaped. In a preferred embodiment the substrate is a cup-shaped plastic vessel or tube of polystyrene, polypropylene, polyethylene, polyvinyl, or polycarbonate, or a combination thereof. In a particularly preferred embodiment the substrate is an optically clear polystyrene microtiter well.

The coating material comprises a polymer of hexosamine, in a preferred embodiment the coating material is a copolymer of galactosamine and glucosamine, either natural or synthetic. In a particularly preferred embodiment the coating material is comprised of chitosan, a derivative of chitin. The coating material further comprises an organic acid. The acid will solubilize chitosan preventing aggregation during coating. Acetic acid will solubilize chitosan, however, the volatile nature of acetic acid results in incomplete coatings, storage difficulties, and residual acetic acid acts aggressively against some antigens and antisera. In an embodiment polyvalent organic acids such as citric acid, malic acid, fumaric acid, aspartic acid, oxaloacetate, and glutaric acid are preferred. In a preferred embodiment citric acid is used as the counterion. It is an embodiment of this invention that the coating may be enhanced by a subsequent alkaline treatment of the coated surface. In a particularly preferred embodiment the alkaline treatment is done concomitant with the immobilization of the molecule of interest. Sodium carbonate/bicarbonate buffer solutions are an ideal embodiment of this invention.

It is a feature of this invention that more antibody will bind to the chitosan coated plate than will bind to an untreated plate. It is an additional feature of this invention that the chitosan may be reacted in solution with an activated hapten to produce a modified chitosan. This hapten-chitosan complex will coat a substrate with a thin film of hapten.

A particularly novel feature of this invention is the ability of a chitosan coated article to be activated. The addition of oxidizers such as sodium nitrite or sodium hypochlorite will produce a reactive surface that can covalently bind protein, nucleic acids, haptens, and other molecules for subsequent assay. The system allows a wide variety of protein and peptide antigens to be coupled in this manner. Proteins include, but are not limited to antibody, enzyme, structural proteins, membrane proteins, gene products, and synthetic proteins. A particularly novel feature of this invention is the ability of the device to immobilize proteins dissolved in a surfactant. Peptide antigens may be similarly attached. These molecules include peptide hormones such as oxytosin, neuropeptides, angiotensin, interleukins, T-cell peptides, and any other natural or synthetic peptide having a free amine or hydroxyl of interest to practioners of the immunoassay art.

In a particularly preferred embodiment the system described herein is used to immobilize haptens as a surface coating. Haptens that may be bound include drugs or drug analogs such as cannabinoid, morphines, barbituates, sulfa drugs, steroids, estrogens, amphetamines, gentamycin, neomycin, tobramycin and others. Haptens of environmental interest include dioxin, halogenated hydrocarbons, phenolic compounds, pesticides, and industrial residue.

In a particularly preferred embodiment the reagents are combined in a kit comprising a solution of chitosan in citrate buffer, and in a separate vessel, reagents for preparation of sodium nitrite oxidizer. This will enable the end user to chemically bind most proteins, antigens, and haptens to substrates that suit their individual needs. It is believed from the preceding description that one skilled in the art can fully grasp the instant invention and use it to its fullest extent. The references cited in this application are herein incorporated by reference as relevant to the practice of immunoassay technology. The following preferred specific embodiments are given as illustrations of applications of the invention and are not to be construed as limitive of the disclosure in any manner.

The following reagents were used in the course of developing this invention. Sources are given where relevant, otherwise they are of the standard commercial grades available.

Carbonate buffer:
0.05M Solution. Available from Sigma Chemical, St. Louis Mo.
Citrate buffer:
0.1M citric acid pH 2.0.
Chitosan stock solution:
Chitosan, available from Sigma Chemical, St. Louis Mo., at 0.02 g/ml dissolved in citrate buffer and filtered.
Chitosan working solution:
Chitosan stock solution diluted 1 part into 10 parts distilled water.
Sodium nitrite:
A solution of 0.002 g sodium nitrite in 200 mls water.
Glutaraldehyde solution:
A 2% solution of glutaraldehyde in water.
Non-specific blocking solution (NSB solution):
Bovine serum albumin (Intergen, Purchase N.Y.), 1 g, with 0.5 g trehalose added to 200 mls of phosphate buffered saline.
Enzyme conjugate solution:
Goat anti-rabbit IgG conjugated to horseradish peroxide, available from Sigma Chemical, St. Louis Mo., was diluted in NSB solution.
Enzyme substrate:
Tetramethyl benzidine solution was obtained from Kirkegaard and Perry, Gaithersberg Md.

EXAMPLE 1

The ability of chitosan to enhance binding of an antibody was demonstrated. Polystyrene microtiter strips (Dynatech Immulon IV) were contacted with chitosan working solution and oxidized with sodium nitrite solution. An antibody solution, Rabbit IgG in carbonate buffer, was added at concentrations varying from 0 to 200 ug/ml. Similar concentrations were added to untreated microtiter strips. NSB solution was used to inhibit false positives. Resolution of the bound antibody was with enzyme conjugate solution and enzyme substrate solution. The results are represented in TABLE 1.

TABLE I

| Antibody Conc. | IgG Binding Absorbance at 620 nm | |
|---|---|---|
| ug/ml | Chitosan | w/o Chitosan |
| 0 | 0.00 | 0.00 |
| 3 | 0.02 | 0.00 |
| 6 | 0.03 | 0.00 |
| 13 | 0.07 | 0.02 |
| 25 | 0.08 | 0.05 |
| 50 | 0.132 | 0.10 |
| 100 | 0.2 | 0.17 |
| 200 | 0.33 | 0.24 |

EXAMPLE 2

The ability to use chitosan coated articles for the assay of materials other than proteins was examined by producing surface layers of drugs. A polystyrene microtiter well strip was contacted with chitosan working solution and activated with the oxidizer solution. A solution of 1 mg/ml Tobramycin was applied and allowed to react to the surface. Non specific reactions were inhibited with the NSB solution and sera containing anti-tobramycin was contacted with the drug coating at concentrations varying from 0 to 1/640. resolution was with goat anti-rabbit-peroxidase using a TMB enzyme substrate. The results are presented in TABLE 2.

EXAMPLE 3

The utility of the oxidation step was demonstrated by modifying the method to substitute the dialdehyde cross linker glutaraldehyde. A polystyrene microtiter strip was contacted with chitosan working solution, followed by glutaraldehyde solution. A solution of 1 mg/ml Tobramycin was applied and allowed to react to the surface. After NSB solution Rabbit anti-tobramycin serum was added at a dilutions ranging from zero to 1/640 and antibody binding was quantified by enzyme conjugate solution. The results are presented in TABLE 2.

TABLE 2

| Tobramycin Detected (Absorbance 620 nm) | | |
|---|---|---|
| Serum dilution | Oxidation | Glutaraldehyde |
| 1/40 | 0.163 | 0.07 |
| 1/80 | 0.131 | 0.03 |
| 1/160 | 0.10 | 0.02 |
| 1/320 | 0.07 | 0.02 |

EXAMPLE 4

Chitosan modified in solution to produce articles with unique hapten surface properties was developed by reacting chitosan stock solution with an activated ester of the drug sulfamethazine. Sulfamethazine-acetate was formed by the action chloroacetic acid on sulfamethazine under basic conditions. This modified drug was reacted with sulfo-N-hydroxysuccinimide (Pierce Chemical, Rockford Ill.) in the presence of carbodiimide to produce the reactive ester, This ester added at 2 mg/ml to chitosan stock solution reacted with the free amines of chitosan generating a chitosan-hapten derivative. This material was found to have the same substrate modifying properties as chitosan solution with the added benefit that the surface contained hapten moieties. Rabbit anti-sulfamethazine was found to bind to sulfamethazine-chitosan coated articles as shown in TABLE 3.

TABLE 3

| Sulfamethazine-Chitosan Plate Derivitization | |
|---|---|
| Serum Dilution | Absorbance 620 nm |
| 1/200 | 0.53 |
| 1/800 | 0.42 |
| 1/3200 | 0.25 |
| 1/12,800 | 0.19 |
| 1/25,600 | 0.06 |

EXAMPLE 5

The versatility of the methodology described in Example 4 was demonstrated by developing chitosan coated articles to the following compounds:
Chlorampmhenicol
Sulfadimethoxine Sulfathiazole
Morphine
Barbituate
Aflatoxin

EXAMPLE 6

A kit for immobilizing proteins, nucleic acids and drugs to chitosan modified articles was developed with the following components in separate containers:

A) Chitosan Stock solution,

B) 2 mg sodium nitrite pellet,

C) 1 g Bovine Serum Albumin and 0.5 g Trehalose.

When used properly the kit provides the end user the means to immobilize a variety of chemical substances. The following agents have been measured on the kit:

Sulfamethazine (Shown in TABLE 4)
Rabbit IgG
Neomycin
Tobramycin
Gentamycin

TABLE 4

| Sulfamethazine Binding | |
|---|---|
| Serum Dilution | Absorbance 620 nm |
| 1/200 | 0.31 |
| 1/800 | 0.19 |
| 1/6400 | 0.09 |
| 1/25,600 | 0.01 |

What is claimed is:

1. An apparatus for performing an immunoassay comprising:
   a) a substrate;
   b) a surface coating member on said substrate comprising a composition of chitosan, either natural or synthetic, and a polyvalent organic acid;
   c) said chitosan of said surface coating member further reacted with an oxidizer to produce a reactive moiety on said surface member;
   d) an immunochemical reagent member covalently bound to said surface coating member via said reactive moiety, thereby insolubilized on said substrate.

2. The apparatus of claim 1 wherein said substrate comprises a microtiter well.

3. The apparatus according to claim 1 wherein said polyvalent organic acid is selected from the group consisting of citric acid, aspartic acid, malic acid, ascorbic acid, fumaric acid, glutaric acid, and combinations thereof.

4. The apparatus according to claim 1 wherein said immunochemical reagent member comprises antibodies which specifically bind an analyte selected from the group consisting of drugs of abuse, therapeutic drugs, hormones, antibiotics, mycotoxins, xenobiotics, microbial antigens, mammalian antigens, and tumor markers, said reagent member bound to said substrate by said surface coating member.

5. The apparatus of claim 1 wherein said oxidizer is selected from the group consisting of nitrite, hypochlorite, sulfite, and combinations thereof.

6. A kit for performing an immunoassay comprising
   a) a substrate,
   b) a composition for coating said substrate comprising chitosan and a polyvalent organic acid selected from the group consisting of citric acid, aspartic acid, malic acid, ascorbic acid, fumaric acid, glutaric acid, and combinations thereof in a single container;
   c) an oxidizing agent for reaction with the chitosan of said composition selected from the group consisting of nitrite, hypochlorite, sulfite, and combinations thereof in a separate container; and
   d) an agent for inhibiting nonspecific binding reactions on said substrate coated with said composition.

7. An apparatus providing reactive surfaces useful in immunoassay procedures comprising:
   a) a substrate;
   b) a surface coating member comprised of a solution of chitosan and a polyvalent organic acid, said chitosan is covalently bound to a drug, drug hapten or xenobiotic useful in diagnostic screening.

8. The apparatus of claim 7 wherein said substrate comprises a microtiter well.

9. The apparatus of claim 7 wherein said polyvalent organic acid is selected from the group consisting of citric acid, aspartic acid, malic acid, ascorbic acid, fumaric acid, glutaric acid, and combinations thereof.

* * * * *